United States Patent [19]

Söderberg

[11] Patent Number: 4,906,191
[45] Date of Patent: Mar. 6, 1990

[54] DENTAL BRIDGE

[75] Inventor: Per O. Söderberg, Stockholm, Sweden

[73] Assignee: Astra Meditec AB, Mölndal, Sweden

[21] Appl. No.: 207,255

[22] Filed: Jun. 15, 1988

[30] Foreign Application Priority Data

Jun. 25, 1987 [SE] Sweden ................ 8702624

[51] Int. Cl.$^4$ .............................................. A61C 11/00
[52] U.S. Cl. ................................. 433/213; 433/173; 433/214
[58] Field of Search ............... 433/214, 213, 173, 196, 433/199.1, 172, 176

[56] References Cited

U.S. PATENT DOCUMENTS 4,708,654 11/1987 Branemark .................... 433/213
4,744,753 6/1988 Ross ................................ 433/213

FOREIGN PATENT DOCUMENTS

WO85/02337 6/1985 PCT Int'l Appl. ............... 433/174

OTHER PUBLICATIONS

Lundquist and Carlsson: "Maxillary Fixed Prostheses on Osseointegrated Dental Implants", The Journal of Prosthetic Dentistry, 50:262, 1983.
Lekholm: "Clinical Procedures for Treatment with Osseointegrated Dental Implants", The Journal of Prosthetic Dentistry, 50:116, 1983.

Primary Examiner—John J. Wilson
Attorney, Agent, or Firm—White & Case

[57] ABSTRACT

The invention relates to a method and a means for preparation of a dental bridge for a dental prosthesis. The dental bridge is modelled by casting in a mold prepared from a casting model. The casting model is built up in the mouth of the patient by modules (3,6) which are joined together into a unit. A module consists of a metal socket (3) on which a cap (6) with a through hole is mounted. The modules are connected to each other preferably by gluing.

11 Claims, 1 Drawing Sheet

DENTAL BRIDGE

FIELD OF THE INVENTION:

The present invention is related to a method and a means to prepare a dental bridge by casting in a mold, which is prepared from a casting model.

BACKGROUND OF THE INVENTION:

An implant is used as an anchoring means for fixing a dental prosthesis when other fixing possibilities are lacking. Building up a dental prosthesis with this type of anchorage is initiated by an insertion by an operation of bone-fixtures in the jaw by making an incision in the gums and drilling bores in the jaw-bone, into which bores bone-fixtures in the form of root screws with a threaded, internal hole are screwed. A cover screw is placed in the internal hole of the root screw whereupon the gums are replaced. After a period of four to six months the implant has been osseointegrated with the jaw-bone and the cover screw is again uncovered and replaced by a spacing element, a pillar. The pillar is healed in under protection of a healing cap.

After completed healing the healing cap is removed and sockets are placed on the pillars and attached to said pillars with internal screws. After sealing of the open ends of the sockets, an impression of the jaw is made by depressing an impression tray filled with impression material on the jaw and the material is allowed to solidify. The upper ends of the sockets are uncovered from impression material and the internal screw is released. The solidified impression including the cast in sockets can now be removed and forwarded to a dental technician.

The dental technician builds up a positive working model of the jaw by, as a first step, attaching pillar dummies into the sockets which are cast in to the model and as a second step making an impression. The screws are released and the positive working model of the jaw in which pillar dummies are cast in can now be used to build up a dental bridge structure. On the pillar dummies, sockets are attached by screws and a continuous bridge structure, a wax model, is modelled of wax or plastic material. The wax model or the casting model must now be forwarded back to the dentist and tested on the patient to check that the matching to the anchoring elements is exact.

When the casting model is back with the dental technician, said model is used for preparation of a mold. This is prepared by pressing the model into a mold compound and burning the wax or plastic material out in a burning oven. A metal framework is cast in the completed mold to form a dental bridge into which the sockets are cast.

The method described above is complicated and suffers from certain disadvantages. Solely to build up the mold, two separate appointments with the dentist and in between work by the dental technician are needed. It has also been experienced that the completed casting model, when tested on the patient, often does not match exactly, which causes further treatments and subsequent adjustments. One disadvantage in this method is also the casting of the impression inside the mouth which is extremely unpleasant for the patient.

SUMMARY OF THE INVENTION:

The object of the present invention is to simplify the preparation of a dental bridge as described above by way of introduction and the method according to the invention is characterized in that the casting model is built up in the mouth of the patient by modules which are joined together.

The means for carrying out the above method is characterized by a module which comprises a prefabricated cap with a through hole.

Further advantageous features of the invention will become apparent from the following description of one embodiment of the invention and from the dependent claims.

According to the invention the advantage of a simplified preparation method of the casting model is obtained, which model is modelled during one single appointment with the dentist and without contribution of a dental technician. The risk for a defective fit in the workmanship is completely eliminated by this method. A further advantage is lack of impressions in the mouth which are unpleasant for the patient.

BRIEF DESCRIPTION OF THE DRAWINGS:

The invention is described in detail with reference to the accompanying drawings, where.

Figure 1:
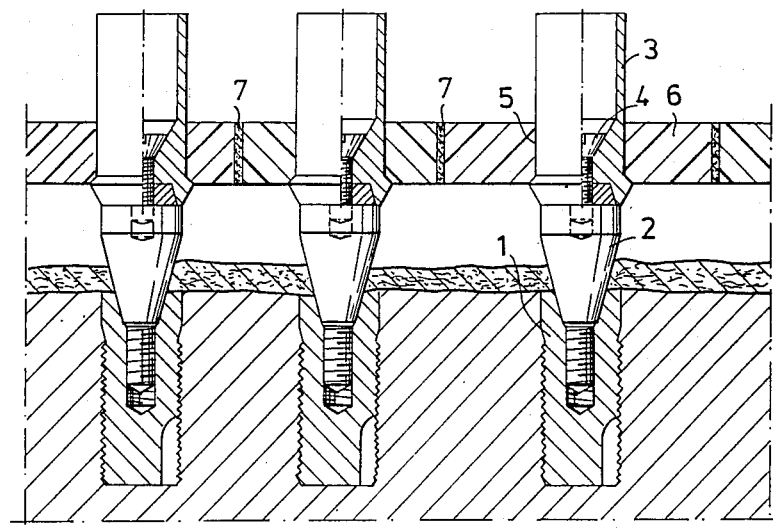
FIG. 1 shows a longitudinal section through a section of the jaw during modelling of the casting model.
Figure 2:
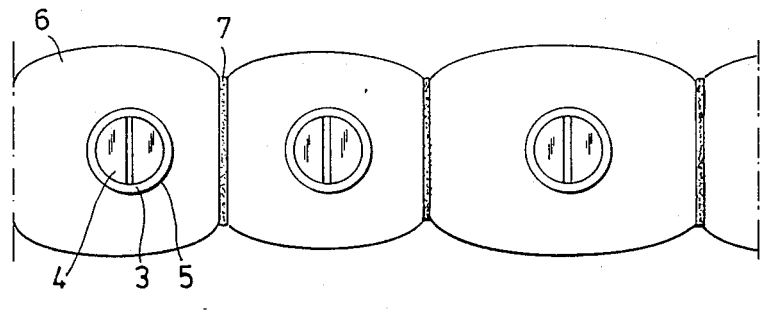
FIG. 2 shows from above a section of the jaw with joined modules according to FIG. 1.

DETAILED DESCRIPTION OF A PREFERRED EMBODIMENT OF THE INVENTION:

In FIG. 1 a number of root elements 1 are shown, which are screwed and osseointegrated in the jaw-bone. In each of the internal holes of the root screws 1 a pillar 2 is screwed in, said root screw 1 and said pillar 2 together form anchoring elements for the bridge structure. On the conical upper end of the pillar 2, a metal socket 3 is fitted and attached to the pillar with an internal screw 4. A prefabricated cap 6 is arranged and affixed on the socket 3, said cap having a through hole 5 with a shape and a size corresponding to the metal socket 3. The cap 6 is preferably made of burnable plastic material. The external shape of the cap 6 is somewhat rounded (see FIG. 2) with two diametrically opposed and flat surfaces. The flat surfaces of the adjacent caps are arranged parallel with each other to form a gap 7 of suitably uniform thickness between the flat surfaces. The gap 7 is filled up with burnable glue. The modules are thus joined together by these glue joints 7 to form a continuous unit.

The method for preparation of a dental bridge according to the invention is as follows:

When the anchoring elements, each comprising a root screw 1 and a pillar 2, have been osseointegrated with the jaw-bone and healed in, the healing cap is removed as described above. The prefabricated cap 6, preferably made of plastic material which can be burnt out, is mounted around the socket 3 and the two units 6, 3 are affixed to each other with burnable glue. The socket 3 with the cap 6 is placed and fitted on the conical surface of the pillar 2 in the mouth of the patient and is attached to the pillar 2 with the internal screw 4.

In the same way another cap 6 is mounted around the following socket 3 and the unit is placed on the adjacent pillar 2. Before the socket 3 is fastened with a screw in its position, the cap 6 is trimmed for the purpose of achieving a suitable space between the adjacent caps to form a gap 7 for the glue. The trimming comprises either grinding of the flat surface or building up the surface by application of burnable plastic material, depending on the distance between the anchoring elements in the jaw-bone. After the trimming the socket 3 is thus fastened with a screw and the following socket with cap is subjected to the same procedure. When all the pillars have been provided with a socket 3 and a cap 6 in the described way, the whole system is joined together by application of burnable glue in each gap 7.

The modelling of the casting model has so far been made by the dentist (dental prosthetist) in the mouth of the patient during one single appointment. As the model is built up on the actual anchoring elements in the mouth of the patient instead of on pillar dummies which are cast in a positive model of the jaw, the risk of defective fitting and subsequent adjustments is eliminated.

The internal screws of the sockets can now be released and the casting model can be lifted out and forwarded to the dental technician. The dental technician provides the model with retention means and forms the mold in a customary way by pressing the casting model into a mold compound and burning the plastic material out whereby the dental bridge is cast.

POSSIBLE MODIFICATIONS OF THE INVENTION:

The invention is in no way limited to the embodiment described above and several possible modifications of the invention are possible within the scope of the claims. The internal and external shape of the caps can vary, as far as the internal through hole is given a shape which corresponds to the external shape of the socket, which shape can differ from the cylindrical shape which is shown in the figures. To facilitate and minimize the trimming, the plastic cap can be manufactured and provided in several different sizes. In this way the dentist can choose a size of the cap which will fit the distance between the anchoring elements in the jawbone. Instead of trimming adjustments, different spacing elements made of burnable plastic material can be affixed between the caps.

I claim:

1. In a method of preparing a dental bridge of the type that is affixed to a plurality of osseointegrated anchoring elements implanted in a jawbone, such method including the step wherein the bridge is prepared by casting in a mold made from a casting model, the improvement wherein the casting mode is produced in place on the anchoring elements by the steps of temporarily fastening to each of the plurality of anchoring elements a socket fitted with a prefabricated modular cap, the caps being sized such that a gap is left between adjacent caps, and joining the adjacent caps into a unit.

2. The improvement according to claim 1 wherein the caps are joined into a unit by applying an adhesive in the gaps between caps, wherein the sockets are of metal and are adapted to form part of the bridge, and wherein the caps and adhesive are of a material adapted to be removed in preparing the mold for the dental bridge, leaving the sockets in the mold.

3. The improvement according to claim 1 and further comprising the step of sizing the adjacent caps to form gaps between them that are suitable for forming adhesive joints between them.

4. The improvement according to claim 3 where in the caps are sized by grinding off material at a surface forming the gap.

5. The improvement according to claim 3 wherein the caps are sized by adhesively bonding spacing elements to them along surfaces adjacent the gaps.

6. A casting model for use in preparing a mold for a dental bridge of the type that is affixed to a plurality of osseointegrated anchoring elements implanted in a jawbone comprising a plurality of sockets adapted to be removably affixed to the anchoring elements, a prefabricated cap received on each socket and forming a gap with an adjacent socket, and means disposed in the gaps between adjacent caps for joining the caps into a unit.

7. A casting model according to claim 6 wherein the means for joining the caps are adhesive joints.

8. A casting model according to claim 7 wherein the caps and the adhesive of the joints are of materials adapted to be destroyed when the mold for the bridge is made from the casting model.

9. A casting model according to claim 7 wherein the sockets are metal and are adapted to be cast into the bridge.

10. A casting model according to claim 9 wherein the caps and the adhesive of the joints are burnable.

11. A casting model according to claim 6 wherein the caps are selected individually from a supply containing several different sizes such as to form gaps suitable for forming the adhesive joints.

* * * * *